US010492753B2

(12) United States Patent
Kagermeier et al.

(10) Patent No.: US 10,492,753 B2
(45) Date of Patent: Dec. 3, 2019

(54) METHOD AND OPERATING SYSTEM FOR CONTROLLING A MEDICAL TECHNOLOGY FACILITY WITH A MOVABLE COMPONENT

(71) Applicant: Siemens Healthcare GmbH, Erlangen (DE)

(72) Inventors: Robert Kagermeier, Nuremberg (DE); Gerben Ten Cate, Forchheim (DE); Asa MacWilliams, Fuerstenfeldbruck (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/190,275

(22) Filed: Nov. 14, 2018

(65) Prior Publication Data

US 2019/0150875 A1 May 23, 2019

(30) Foreign Application Priority Data

Nov. 17, 2017 (DE) ........................ 10 2017 220 532

(51) Int. Cl.
*A61B 6/00* (2006.01)
*G06F 3/01* (2006.01)
(Continued)

(52) U.S. Cl.
CPC ............ *A61B 6/548* (2013.01); *A61B 6/0407* (2013.01); *A61B 6/547* (2013.01); *G06F 3/017* (2013.01);
(Continued)

(58) Field of Classification Search
CPC ..... A61B 6/548; A61B 6/0407; A61B 6/4441; A61B 6/547; A61B 2090/3945;
(Continued)

(56) References Cited

U.S. PATENT DOCUMENTS

2012/0201355 A1* 8/2012 Butzine .................. A61B 6/544 378/62
2014/0016751 A1 1/2014 Sung et al.

FOREIGN PATENT DOCUMENTS

EP 2684522 A1 1/2014

OTHER PUBLICATIONS

German Office Action for German Application No. 102017220532.6 dated Jul. 17, 2018 and English Translation thereof.

* cited by examiner

*Primary Examiner* — Courtney D Thomas
(74) *Attorney, Agent, or Firm* — Harness, Dickey & Pierce, P.L.C.

(57) ABSTRACT

A method is for controlling an imaging device including at least one component, movable according to an operator input via a smart device including at least one smart device sensor. The method includes recording, via the at least one smart device sensor, sensor data defining at least one of movement and position of the smart device in a space of the imaging device where the smart device is situated; determining, from the sensor data recorded, position data defining the position and an orientation of the smart device relative to the at least one component, and/or movement data defining a movement relative to the at least one component; and evaluating the at least one of position data and movement data to select at least one of the at least one component, and/or determine an operator input in relation to at least one of the at least one component.

20 Claims, 3 Drawing Sheets

9
20
9
9
15
14
16
18
1
2
19
21
22
5
17

(51) Int. Cl.

| | |
|---|---|
| ***G06F 3/03*** | (2006.01) |
| ***G06T 7/246*** | (2017.01) |
| ***G06T 7/73*** | (2017.01) |
| ***A61B 6/04*** | (2006.01) |
| ***G06F 3/0346*** | (2013.01) |
| *A61B 90/00* | (2016.01) |
| *H04W 4/80* | (2018.01) |
| *A61B 6/06* | (2006.01) |
| *H04W 4/02* | (2018.01) |

(52) U.S. Cl.

CPC .......... *G06F 3/0304* (2013.01); *G06F 3/0346* (2013.01); *G06T 7/246* (2017.01); *G06T 7/73* (2017.01); *A61B 6/06* (2013.01); *A61B 6/4441* (2013.01); *A61B 2090/3945* (2016.02); *A61B 2090/3979* (2016.02); *A61B 2562/0219* (2013.01); *A61B 2562/0223* (2013.01); *G06T 2207/30204* (2013.01); *H04W 4/026* (2013.01); *H04W 4/80* (2018.02)

(58) Field of Classification Search

CPC .... A61B 2090/3979; A61B 2562/0219; A61B 2562/0223; G06T 7/246; G06T 7/73; G06T 2207/30204; G06F 3/0346

USPC ............................ 378/62, 65, 198, 204, 205

See application file for complete search history.

1
2
5
9
14
15
16
17
18
19
20
21
22

METHOD AND OPERATING SYSTEM FOR CONTROLLING A MEDICAL TECHNOLOGY FACILITY WITH A MOVABLE COMPONENT

PRIORITY STATEMENT

The present application hereby claims priority under 35 U.S.C. § 119 to German patent application number DE 102017220532.6 filed Nov. 17, 2017, the entire contents of which are hereby incorporated herein by reference.

FIELD

Embodiments of the invention generally relates to a method and an operating system for controlling a medical technology facility, in particular an imaging device, having at least one component which is movable according to an operator input at an operating device.

BACKGROUND

A large number of modern medical technology facilities for diagnosis and treatment, in particular medical imaging devices is known in which there exist movable components for the setting of particular examination or treatment processes, in imaging devices, for example, of recording geometries and/or recording regions and/or for adapting to a current patient, movable components exist, for example the recording arrangement or parts thereof, a patient table provided for positioning a patient, and the like. An example of this is, in particular, X-ray devices in which, for example, the X-ray radiator, the detector and/or the patient table are moved remotely controlled close to the patient. Such a remote control of moving components of a medical technology facility should be implemented as easily and intuitively as possible.

For this purpose, it is known in the prior art to use wired or wireless hand operating units which can comprise, for example, membrane keys and/or foot switches. It has been proposed, in particular, to make cursor keys (arrow keys) and/or explicit function keys available on the operating unit for controlling the movement of components. Since various components can be movable in different degrees of freedom, for example both in the x/y/z-direction and also rotationally, there is a large number of different operating keys and/or there are selection keys for the components to be controlled and for the movement type so that the arrow keys for corresponding component movements are activated. This large number of the operating keys and operating processes provided, in particular also for changing the selection of a component to be controlled, requires a high degree of concentration on the operating field and distracts the operator from the actual, patient-oriented settings of the movable components. This known procedure therefore cannot be regarded as either intuitive or convenient. Added thereto is that the operating units used are relatively expensive to develop and manufacture and also have little flexibility with regard to adaptations or amendments.

SUMMARY

At least one embodiment of the invention provides, in comparison thereto, an improved, more intuitive and simpler to use operating capability for movable components of a medical technology facility.

At least one embodiment of the invention is directed to a method for controlling a medical technology facility using a smart device as the operating device including at least one smart device sensor recording sensor data defining the movement and/or the position of the smart device in the space in which the medical technology facility is situated, wherein position data defining the position and the orientation of the smart device relative to the at least one component and/or movement data defining a movement relative to the at least one component is determined from the sensor data and is evaluated for the selection of at least one of the at least one component and/or for determining an operator input in relation to at least one of the at least one component.

At least one embodiment of the invention is directed to a method for controlling an imaging device including at least one component, movable according to an operator input via a smart device, the smart device including at least one smart device sensor, the method comprising:

recording, via the at least one smart device sensor, sensor data defining at least one of movement and position of the smart device in a space of the imaging device where the smart device is situated;

determining, from the sensor data recorded, at least one of
- position data defining the position and an orientation of the smart device relative to the at least one component, and
- movement data defining a movement relative to the at least one component; and evaluating the at least one of position data and movement data to at least one of
- select at least one of the at least one component, and
- determine an operator input in relation to at least one of the at least one component.

In addition to the method, at least one embodiment of the invention also relates to an operating system for controlling a medical technology facility, in particular an X-ray device, having at least one component which is movable according to an operator input at an operating device configured as a smart device, said operating system having a control device of the imaging device and the smart device and being configured to carry out at least one embodiment of the inventive method. All the embodiments relating to the method according to at least one embodiment of the invention can be transferred similarly to at least one embodiment of the inventive operating system with which the above mentioned advantages can therefore also be achieved.

At least one embodiment of the invention is directed to an operating system for controlling an imaging device, including at least one component, movable according to an operator input, the operating system comprising:

a smart device, including at least one smart device sensor; and at least one processor, to control the imaging device and the smart device, the at least one processor being configured to
- record, via the at least one smart device sensor, sensor data defining at least one of movement and position of the smart device in a space of the imaging device where the smart device is situated,
- determine, from the sensor data recorded, at least one of
  - position data defining the position and an orientation of the smart device relative to the at least one component, and
  - movement data defining a movement relative to the at least one component, and
- evaluate the at least one of position data and movement data to at least one of
  - select at least one of the at least one component, and determine an operator input in relation to at least one of the at least one component.

BRIEF DESCRIPTION OF THE DRAWINGS

Further advantages and details of the present invention are disclosed in the following description of exemplary embodiments and by reference to the drawings. In the drawings.

DETAILED DESCRIPTION OF THE EXAMPLE EMBODIMENTS

Figure 1:
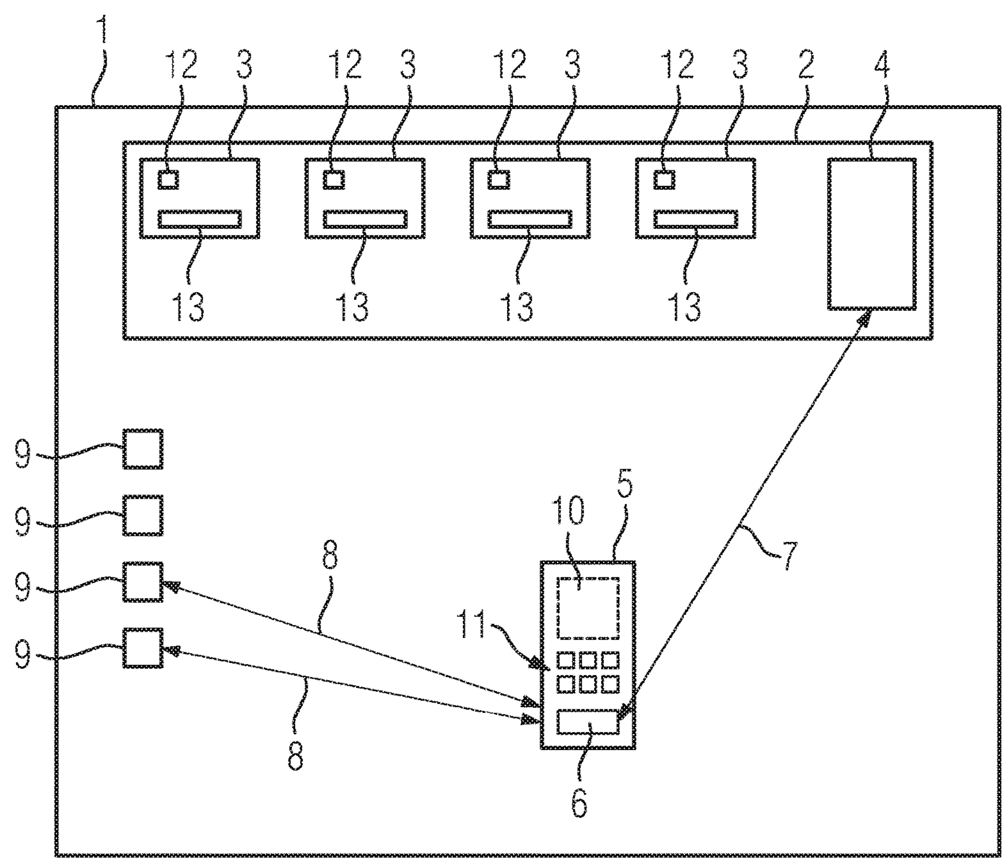
FIG. 1 is a sketch of the principle of components of an operating system according to an embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention is directed to a method for controlling a medical technology facility using a smart device as the operating device including at least one smart device sensor recording sensor data defining the movement and/or the position of the smart device in the space in which the medical technology facility is situated, wherein position data defining the position and the orientation of the smart device relative to the at least one component and/or movement data defining a movement relative to the at least one component is determined from the sensor data and is evaluated for the selection of at least one of the at least one component and/or for determining an operator input in relation to at least one of the at least one component.

A smart device is a hand-held, wireless mobile device which typically has an operating system and is operable via a touch screen which also serves as a display. Typical non-limiting examples of smart devices are smartphones and/or small-format tablets. An intuitive and patient-oriented operation of component movements in medical technology facilities, that is, in particular image recording and/or treatment devices, can be achieved by the use of a commercially available smart device, thus, in particular, a smartphone or a small format tablet. Herein, particularly advantageously, the sensor equipment already present in the smart device can be used to enable a complete orientation and position recognition (and therefore also movement recognition) of the smart device in the space in which the medical technology facility is also situated.

The medical technology facility includes devices for defining current setting information of the at least one component which describes its position in the space, as is known in principle. For example, in a control device of the medical technology facility, the system geometry is just as well known as the current position of the actuators for moving the components, which is determinable, for example, via motor encoders or corresponding sensors. Once the position of the medical technology facility in the space is also known, the relative positions and orientations and/or movements of the at least one component and of the smart device can therefore be determined and evaluated with regard to the remote operation of the at least one component. It is thus in particular possible to point intuitively to components and/or for remote operation of components, to carry out corresponding movements with the smart device, so that operation is possible conveniently and while looking at the components to be controlled. For this purpose, the smart device is preferably configured elongate, in particular having a substantially rectangular and flat basic shape. Thus the smart device can be directed to the components to be operated.

Through the use of a commercially available smart device and the smart device sensors already contained therein, a very cost-effective hand operating system is obtained which is also highly versatile in use. By way of the method proposed here for position, orientation and movement determination, a very intuitive operation of a medical technology facility, in particular thus a medical diagnostic and/or therapeutic system, is obtained.

In an advantageous embodiment of the present invention, it can be provided that at least one smart device sensor is a camera in the image data of which optical markers arranged in the space, the position of which in the space is known, are detected and used for determining the position data and/or the movement data. In particular, it can be provided that the smart device has two cameras, in particular a front camera and a rear camera which on normal use of the smart device are also oriented such that a corresponding quantity of the space and thus the optical markers proposed here can be detected. The markers are continuously recorded and analyzed by the at least one camera typically already present in the smart device, wherein the operator carries the smart device in his natural use and therefore does not need to assume a search position for the camera of the smart device. The position of the respective optical marker in the space can be precisely determined during a configuration phase and made known in the control device executing the evaluation, in particular therefore the control device of the medical technology facility and/or of the control device of the smart device. In concrete terms, it is for example conceivable to use passive optical markers, for example, printed stickers and to apply them to the ceiling, the walls and/or the floor of the space in which the medical technology facility is situated wherein, in particular, an application of optical markers in general onto the medical technology facility itself is also conceivable.

A preferred embodiment of the present invention provides, however, that active markers, in particular comprising optical and/or infrared LEDs, are used as at least a portion of the markers. It is particularly suitable if the active markers are controlled for position determination of the smart device via a short-range radio connection, in particular a Bluetooth connection, for operation. An optimized recognition of the optical markers can thus be achieved with active and synchronized markers (optical beacons). The synchronization can take place via the short-range radio interface also already present in smart devices, for example Bluetooth Low Energy (BLE). With the active control of brightly glowing active markers, in particular brightly glowing infrared LEDs of the markers, a significantly improved recognition of the optical markers can be achieved. These optical markers are or will suitably be synchronized with the smart device sensors, as described.

In this context, a suitable development of an embodiment of the invention provides that the position data is at least partially determined according to a signal transit time method and/or on the basis of a field strength of the radio signals transmitted by the markers with a bidirectional short-range radio connection. If the active markers configured, for example, as optical beacons are configured via a dedicated short-range radio interface for direct communication with the smart device, in addition to the optical marker properties, they also form radio markers (in particular radio beacons) which can already contribute to the at least rough position determination of the smart device in the space, for example, in that the transit time of radio signals and/or their strength is measured. The corresponding field strengths (receiving strengths) in the space can be determined in a configuration phase, as has been proposed, for example, in a BLE beacon concept from the Fujitsu company.

In a suitable development of an embodiment of the invention, it can be provided that the existence and/or the establishment and/or a property of the short-range communication connection are used for detecting whether the smart device is located in the space, in particular for triggering the beginning of the determination of the position data and/or of the movement data. Apart from the position determination, the fact that a short-range radio connection, in particular to the active markers, is creatable also for activating the precise position and/or movement acquisition are used as a trigger. This means that only when the smart device recognizes that it is at the medical technology facility, it starts the recognition and possibly also the connection establishment to a control device of the medical technology facility. In this way, otherwise a range restriction of the mobile smart device can also be established.

In one embodiment, also, in which no short-range radio connection to active optical markers is established, a similar functionality can be enabled with a rough position determination. In this case, the actively light-emitting optical markers can be operated as light beacons. To achieve this, it can be provided that the actively light-emitting optical markers emit a marker-specific identification signal modulated to the light, which is evaluated by the receiving smart device. On the basis of the identification signals detected in the sensor data of the camera, a first rough position determination can take place. The detection of such identification signals can also be used for detecting whether the smart device is located in the space, in particular for triggering the beginning of the determination of the position data and/or of the movement data. Such technology has already been proposed for localization in supermarkets by the Philips company (white paper: “Indoor positioning”).

Preferably and, in particular, in addition to the at least one camera, at least one acceleration sensor and/or at least one rotary speed sensor and/or at least one magnetic field sensor, in particular as a compass, can be used as the smart device sensor wherein, in particular, the position data and/or the movement data is determined at least partially by way of dead reckoning navigation. In particular with regard to the determination of an orientation and/or the movement, taking into account such preferably further smart device sensor systems is suitable. For example, by way of the evaluation of the acceleration and/or rotary speed sensor, a pivoting and/or tilting of the smart device can be established. A magnetic field sensor which functions, in particular as a compass, provides the additional information of the rough north direction, which can also be taken into account. It is particularly suitable in the context of the present invention if the following of the orientation and position of the smart device is supported by dead reckoning (inertial) navigation. If, for example, the optical marker recognition is temporarily prevented by unfavorable angles of view or if it is hindered, nevertheless, the position data and the movement data can still be determined.

In principle, it is possible within the scope of embodiments of the present invention, particularly in the case of a plurality of components, to select the component to be operated via a display, in particular the touch screen of the smart device. However, this is less preferable.

In contrast thereto, a particularly preferable embodiment of the present invention provides that for the selection of a component to be controlled, the orientation of the mobile device contained within the position data is evaluated as to whether the operator is pointing with the mobile device at one of the at least one component which, in particular after actuation by the operator of a confirmation operating device (s), is selected. In this embodiment, the operator therefore directs the smart device toward the component to be operated in order to select it and to relate subsequent operator input to this component. Herein, for example, the longitudinal axis of the smart device which is known on the basis of the position data can be extended and it can be tested which component it (first) touches. This enables a particularly intuitive selection.

It is now conceivable in one embodiment, in particular by reverse communication to the smart device, to display the selected component on a display, in particular the touch screen, of the smart device. In a particularly advantageous, preferred embodiment, however, the selection of a component can be indicated by at least one optical output device arranged on the selected component, in particular an LED band and/or a backlightable colored area. In this case, the medical technology facility, specifically the at least one component, has activatable optical markings, for example colored areas and/or LED bands with which as an output device, it can be directly visually indicated to the operator which component is currently being selected by him. By this, it is advantageously prevented that the operator turns his gaze away from the component being targeted and has to look at the relatively small display of the smart device, which would entail an unpleasant change of focus.

It is further particularly preferred embodiment in the context of the present invention if the movement of a selected one of the at least one component takes place according to the movement of the smart device on the basis of movement data as operator input. If firstly, particularly given a plurality of components, one of these components is selected for displacement, in particular by targeting with the smart device, the desired movement direction/movement type can be interpreted at the smart device, for example so that in the case of a left swipe of the smart device, the user also brings about a corresponding leftward movement of the selected component, regardless of whether the user is situated in front of, laterally from or behind the component. In this way, a high-quality intuitive setting of components of the medical technology facility is possible once, in particular, the corresponding degrees of freedom of movement can be directly represented by the smart device. If a degree of freedom of movement is, for example, not available, this can be indicated by a corresponding feedback to the user; otherwise, on the basis of the known position data and movement data of the smart device, the movement can be correspondingly converted, from the viewpoint of the user, into a movement of the component, which in particular can also be converted with regard to combined movements, by a plurality of actuators, for example pivoting about a central axis; naturally, it is also conceivable, for example on pivoting and/or linear movements, correspondingly to select the nearest degree of freedom of movement of the component.

Particularly advantageous herein is the embodiment in which the selection of the component to be controlled takes place by pointing with the smart device at the component, whereupon corresponding movements of the smart device can be converted into movements of this selected component. It should also be noted at this point that in relation to movements close to the patient and possible collision risks, in the context of an embodiment of the invention, in principle, known collision protection systems can naturally also be used in addition to the operating concept described here.

It should further be noted that by way of these control functions in an X-ray device, the size and shape of the X-ray beam limiting setting can also be remotely controlled with regard both to the selection of the X-ray beam limiting device and also the change, once for example it is possible to point to a beam limiting element or the beam limiting device itself and one or the other can be displaced, as it were, remotely by the smart device.

In concrete terms, it can be provided for the movement that for receiving an operator input by the mobile device, an actuation of an operating device(s) of the mobile device, in particular a movement release button, is checked. This means that following selection of a component, not every movement with the smart device must necessarily lead to a (possibly undesired) movement of the component, but the operator can signify his intention to undertake a displacement via a corresponding simple operating device(s) on the smart device which can be realized via the touch screen, but can also use an additional button on the smart device, which is possible in particular without directing the gaze to the smart device itself and therefore without it being averted from the actual adjustment procedure. In this way, the safety is increased without compromising the intuitiveness and simplicity of the method described here.

In a further development of an embodiment of the invention, it can be provided that an operator input defining a target position as the position currently aimed by the smart device is accepted on actuation of a target selection operating device(s), in particular a target selection button, wherein a selected component of the at least one component is moved to the target position. It is therefore also conceivable within the scope of the present invention, by way of the pointing direction of the smart device, to define a desired target position which can subsequently be approached automatically on actuation of a corresponding operating device(s).

The determination of the position data and/or of the movement data and also the control operation following therefrom can be realized at different positions in the overall operating system and/or distributed. It can thus be provided that the position data and/or the movement data is determined by a control device of the medical technology facility and/or by a control device of the smart device. While it is certainly conceivable to use the smart device itself to determine at least the position in the space and/or the movement, it is preferable to use a control device of the medical technology facility communicating with the smart device, due to its more available resources. Different types of communication connections can be used, in particular again a short-range radio connection and/or a WLAN connection and/or the like.

In a concrete embodiment of the invention in an X-ray device as the medical technology facility, as the components, a patient table and/or an X-ray radiator and/or an X-ray detector and/or a C-arm and/or a beam limiting device can be used. Naturally, a large number of other movable/adjustable components that can be controlled via the smart device in an intuitive and simple manner is also conceivable.

In addition to the method, at least one embodiment of the invention also relates to an operating system for controlling a medical technology facility, in particular an X-ray device, having at least one component which is movable according to an operator input at an operating device configured as a smart device, said operating system having a control device of the imaging device and the smart device and being configured to carry out at least one embodiment of the inventive method. All the embodiments relating to the method according to at least one embodiment of the invention can be transferred similarly to at least one embodiment of the inventive operating system with which the above mentioned advantages can therefore also be achieved.

FIG. 1 shows a sketch of the principle of an exemplary embodiment of an operating system according to the invention. Arranged in a space 1 is a medical technology facility 2, in this case an imaging device configured as an X-ray device. The medical technology facility 2 comprises a plurality of components 3 movable via remote control, in the present exemplary embodiment, comprising an X-ray radiator, an X-ray detector, a patient table and a beam limiting device. The operation of the medical technology facility 2 is controlled by a corresponding control device 4.

As an operating device for the medical technology facility 2, in particular for the movable components 3, the operating system also comprises a smart device 5 configured herein as a smartphone, of which the control device 6 can establish a wireless communication connection 7 to the control device 4 via a corresponding radio interface (not shown in detail), in particular a Bluetooth interface and/or a WLAN interface. The Bluetooth interface, where herein Bluetooth Low Energy (BLE) is used, is also used to establish short-range radio connections 8 to at least a portion of optical markers 9, in concrete terms at least to active optical markers 9 which therefore can be controlled for the output of optical signals that are to be detected.

It should be noted that the possibility for the establishment of the short-range radio connections 8 or their properties can also be used as a general trigger which indicates that the smart device 5 is situated in the space 1 and specifically can therefore be used for controlling the medical technology facility 2. On the basis of this trigger, for example, the establishment of the communication connection 7 can be triggered and/or a more precise position determination which is described in greater detail below, can be initiated. Alternatively, via the camera, identification signals modulated onto the actively emitted light from markers 9 acting as light beacons can be recorded and evaluated to determine whether the smart device 5 is in the space 1.

The smart device 5 also comprises, as is known in principle, a touch screen 10 as an operating device(s) and display. Furthermore, the smart device 5 has smart device sensors 11, in the present case two cameras, specifically a front camera and a rear camera, acceleration sensors, rotary speed sensors and a magnetic field sensor which acts as a compass.

Actuators 12 drivable, firstly, by the control device 4 for providing the movability, for example motors, are assigned to the remotely movable components 3, said actuators otherwise also feeding back their respective position to the control device 4, so that it constantly knows the position of the components 3 due to the system geometry of the medical technology facility 2 which is also known to it. The control device 4 also knows the position of the medical technology facility 2 in the space 1. If the position and orientation or the movement of the smart device 5 in the space 1 can be determined as corresponding position data or movement data, it can be placed into relation with the respective components 3, in particular through a selection of a component 3 to be operated and a specification of a movement to be performed as operator input which is then converted accordingly by the actuators 12.

In order to indicate, without the operator having to avert his gaze from the components 3, that a component 3 has been selected, the latter also have output devices 13, for example LED bands the illumination of which clearly indicates that the respective component has been selected for operation, as described in greater detail below.

In order to determine the orientation, position and also movement of the smart device 5 in the space 1, the smart device sensors 11, in particular the markers 9 detectable by the cameras are used.

Figure 2:
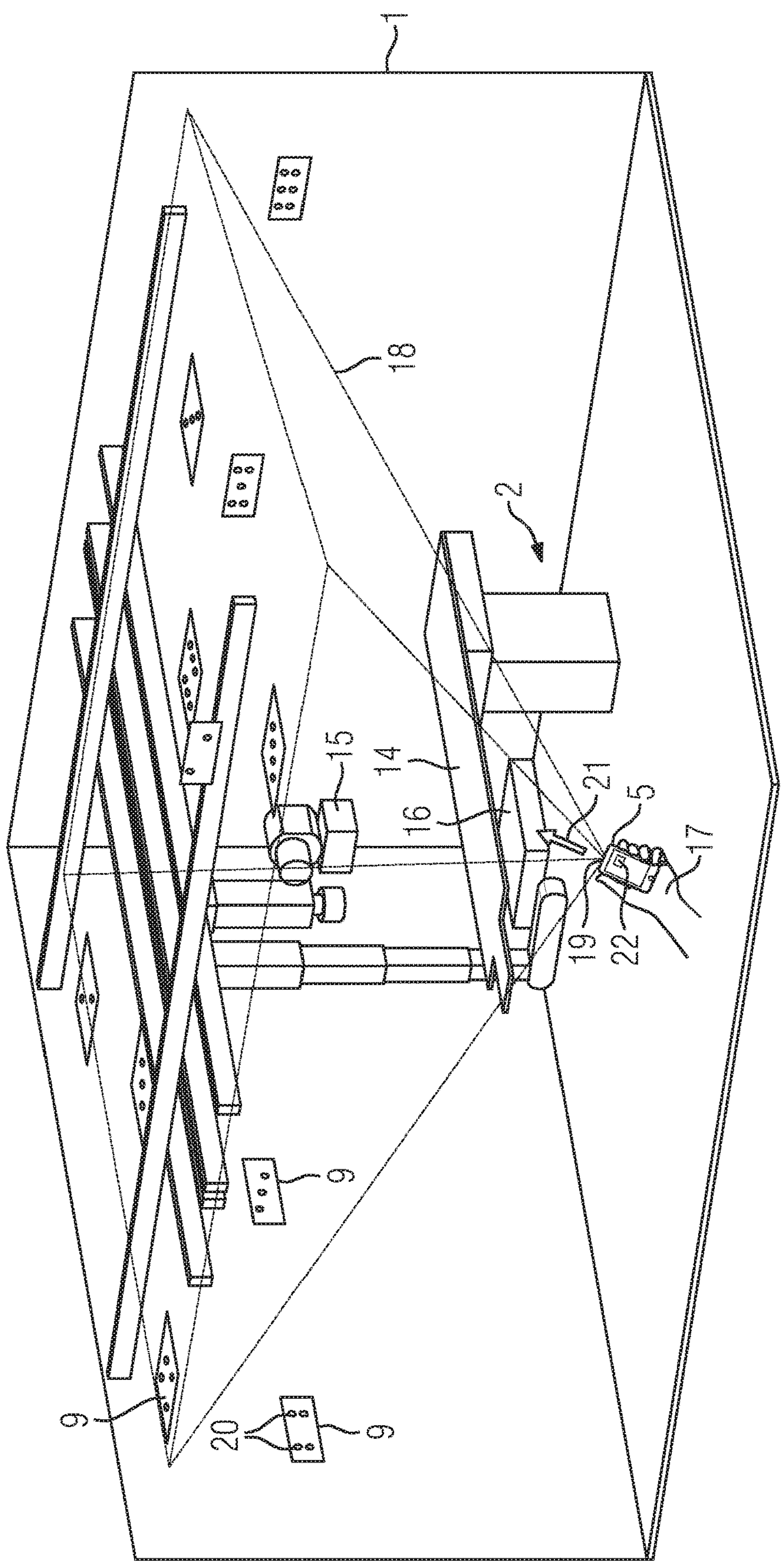
FIG. 2 is a representation to illustrate the localization via markers and a camera of a smart device.

FIG. 2 illustrates this more precisely in the form of a perspective view of the space 1. Visible firstly are the medical technology facility 2 with the patient table 14, the X-ray radiator 15 and the X-ray detector 16 as components 3; a beam limiting device is not shown in the interests of clarity. A hand 17 of an operator holds the smart device 5 in the space, the detection region 18 of the front camera 19 being indicated as the smart device sensor 11. The markers 9 clearly distinguishable in their optically perceptible patterns are visible at different positions in the space 1, in the present case for the sake of clarity, distributed at least on the ceiling and the walls; an arrangement of optical markers 9 on the floor is naturally also possible. The active markers 9 here have infrared LEDs 20 in different patterns.

Since the smart device 5 is elongate, lying in the hand 17 it has a clearly defined pointing direction 21, symbolized by an arrow, specifically the extension of the longitudinal axis of the smart device 5.

In operation for controlling components 3, via the control device 4 and/or the control device 6, position data and movement data of the smart device 5 is continuously generated. Since the position and the properties of the markers 9 in a configuration phase is determined and stored, for example, in a database, the markers 9 detected by the camera 19 can serve for position determination, wherein the active markers 9 are controlled via the corresponding short-range radio connections 8, in synchronization with the smart device 5, to emit correspondingly detectable signals. The infrared LEDs 20 enable a reliable recognition of the markers 9. On the basis of the short-range radio connection 8, the active markers 9 also act as radio beacons, which enables at least a rough position determination (with transit time and field strength measurements). In support of the sensor data of the camera, the sensor data of the acceleration sensors (tilting in the space), of the rotary speed sensors (movement) and the magnetic field sensors (orientation relative to north roughly determinable) are taken into account.

Figure 3:
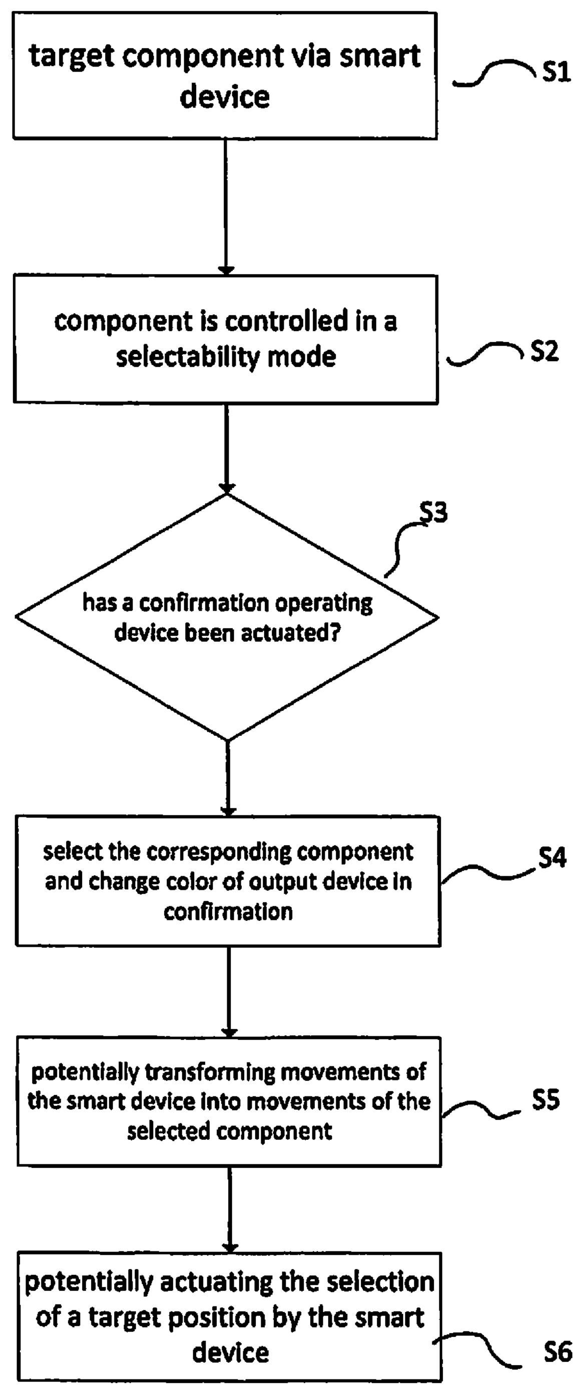
FIG. 3 is a flow diagram of an operating action in an embodiment of the inventive method.

FIG. 3 illustrates a possible operating procedure of a component 3 in more detail.

In a step S1, the operator targets the component 3 to be controlled, via the smart device 5. From the current position data, the extension of the longitudinal axis, that is the pointing direction 21, can be determined so that it can be checked whether the smart device 5 is pointing at a component 3. If this is the case, in a step S2, the output device 13 assigned to this component is controlled in a selectability mode, for example, for emitting a first color. If, then in a step S3, it is determined that a confirmation operating device(s), in the present case displayed on the touch screen 10, has been actuated, the corresponding component is finally selected in a step S4 as to be operated and the output light of the output device 13 changes color in confirmation, for example, from yellow to green.

In a step S5, the possibility exists, by way of a further operating device displayed on the touch screen 10, in this case a movement release button 22 (see FIG. 2), of transforming movements of the smart device 5 into movements of the selected component 3. If, in FIG. 2, for example the X-ray emitter 15 has been selected and if the smart device 5 is moved to the right, the X-ray emitter 15 also moves to the right, provided the movement release button 22 has been actuated. A similar principle applies for rotations and other movements, provided these degrees of freedom of movement are available.

A step S6 symbolizes a further possibility for the remote control of a component 3, specifically the selection of a target position by the smart device 5 in that this is pointed at and a target selection operating device(s), which can also be displayed on the touch screen 10, is actuated. The component 3 is then moved to the corresponding target position.

In addition, a deselection device(s) or a re-selection operating device(s) can also be provided in order to mark a further component 3 for control. Furthermore, components 3 can naturally also be coupled to one another, for example, where the X-ray detector 16 and the X-ray radiator 15 are concerned, at least with regard to some degrees of freedom of movement. This is all implemented in the control device 4.

It should finally be noted that when, for example, the markers 9 are not or are insufficiently recognizable due to unfavorable angles of view, a dead reckoning navigation method by way of the acceleration sensors and the rotary speed sensors can take place.

Although the invention has been illustrated and described in detail with the example embodiments, the invention is not restricted by the examples given and other variations can be derived therefrom by a person skilled in the art without departing from the protective scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase “means for” or, in the case of a method claim, using the phrases “operation for” or “step for.”

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE CHARACTERS

1 Space
2 Medical technology facility
3 Components
4 Control device
5 Smart device
6 Control device
7 Communication connection
8 Short-range radio connection
9 Markers
10 Touch screen
11 Smart device sensor
12 Actuator
13 Output devices
14 Patient table
15 X-ray radiator
16 X-ray detector
17 Hand
18 Detection region
19 Camera
20 Infrared LED
21 Pointing direction
22 Movement release button
S1 Step
S2 Step
S3 Step
S4 Step
S5 Step
S6 Step

What is claimed is:

1. A method for controlling an imaging device including at least one component, which is movable according to input via a smart device, the smart device including at least one smart device sensor, the method comprising:

recording sensor data via the at least one smart device sensor, the sensor data defining at least one of movement or a position of the smart device in a space in which the smart device is situated;

determining at least one of position data or movement data based on, the sensor data, the position data defining an orientation and the position of the smart device relative to the at least one component, and the movement data defining movement of the smart device relative to the at least one component; and evaluating the at least one of position data or movement data to at least one of select at least one of the at least one component, or determine an input in relation to at least one of the at least one component; wherein the at least one smart device sensor includes a camera; and optical markers, arranged in the space, are detectable and usable for the determining at least one of position data or movement data.

2. The method of claim 1, wherein at least a portion of the optical markers include active markers.

3. The method as claimed in claim 2, wherein the active markers are controllable for determining the position of the smart device via a short-range communication connection.

4. The method as claimed in claim 3, wherein the determining at least one of position data or movement data at least partially determines the position data according to at least one of a signal transit time method or a field strength of radio signals transmitted by the active markers with a bidirectional short-range communication connection.

5. The method of claim 3, further comprising:

detecting whether the smart device is located in the space using the short-range communication connection.

6. The method of claim 1, wherein the at least one smart device sensor includes at least one of at least one acceleration sensor, at least one rotary speed sensor, or at least one magnetic field sensor; and the determining at least partially determines the at least one of position data or movement data via dead reckoning navigation.

7. The method of claim 1, wherein the position data includes an orientation of the smart device; and the evaluating the at least one of position data or movement data includes selecting the at least one component, and evaluating the orientation of the smart device to determine whether an operator is pointing, with the smart device, at a component among the selected at least one component selected.

8. The method of claim 7, further comprising:

indicating selection of the at least one component by at least one optical output device arranged on the selected at least one component.

9. The method of claim 1, wherein the evaluating the at least one of position data or movement data comprises:

evaluating the movement data to select the at least one component based on movement data input by an operator according to movement of the smart device.

10. The method of claim 9, further comprising:

receiving the input by checking an actuation of an operating device of the smart device.

11. The method of claim 1, further comprising:

accepting input defining a target position as a position at which the smart device is currently aimed in response to actuation of a target selection operating device; and moving a selected component, from among the at least one component, to the target position.

12. The method of claim 1, wherein the imaging device is an X-ray device and the at least one component includes at least one of a patient table, an X-ray radiator, an X-ray detector, a C-arm, or a beam limiting device.

13. The method of claim 1, wherein the at least one of position data or movement data is effected by a control device of at least one of the imaging device or the smart device.

14. The method of claim 1, wherein the imaging device is an X-ray device.

15. The method of claim 2, wherein the active markers include optical light emitting diodes (LEDs), infrared LEDs or a combination of at least one optical LED and at least one infrared LED.

16. An operating system for controlling an imaging device including at least one component, the at least one component movable according to input, the operating system comprising:

a smart device including at least one smart device sensor; and at least one processor to control the imaging device and the smart device, the at least one processor being configured to execute computer-readable instructions to record sensor data via the at least one smart device sensor, the sensor data defining at least one of movement or a position of the smart device in a space in which the smart device is situated, determine at least one of position data or movement data based on the sensor data, the position data defining an orientation and the position of the smart device relative to the at least one component, and the movement data defining movement of the smart device relative to the at least one component, and evaluate the at least one of position data or movement data to at least one of select at least one of the at least one component, or determine an input in relation to at least one of the at least one component; wherein the at least one smart device sensor includes a camera; and optical markers, arranged in the space, are detectable and usable for determining the at least one of position data or movement data.

17. The operating system of claim 16, wherein the imaging device is an X-ray device.

18. The operating system claim 16, wherein the position data includes an orientation of the smart device; and the at least one processor is configured to execute the computer-readable instructions to select the at least one component, and evaluate the orientation of the smart device to determine whether the operator is pointing the smart device at a component among the selected at least one component.

19. The operating system of claim 16, wherein at least a portion of the optical markers include active markers;

the active markers are controllable for determining the position of the smart device via a short-range communication connection; and the at least one processor is configured to execute the computer-readable instructions to at least partially determine the position data according to at least one of a signal transit time method or a field strength of radio signals transmitted by the active markers with a bidirectional short-range communication connection.

20. The operating system of claim 16, wherein the at least one processor is further configured to execute the computer-readable instructions to accept input defining a target position as a position at which the smart device is currently aimed in response to actuation of a target selection operating device; and move a selected component, from among the at least one component, to the target position.

* * * * *